United States Patent
Boehm et al.

(10) Patent No.: US 9,095,399 B2
(45) Date of Patent: Aug. 4, 2015

(54) DENTAL PACKAGE, AND METHOD OF MAKING THE PACKAGE

(75) Inventors: Andreas Johannes Boehm, Reichling (DE); Marc Peuker, Schöndorf (DE); Bruce R. Broyles, Oakdale, MN (US); Dieter Poschmann, Starnberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 718 days.

(21) Appl. No.: 12/812,980

(22) PCT Filed: Jan. 20, 2009

(86) PCT No.: PCT/US2009/031432
§ 371 (c)(1),
(2), (4) Date: Mar. 31, 2011

(87) PCT Pub. No.: WO2009/094330
PCT Pub. Date: Jul. 30, 2009

(65) Prior Publication Data
US 2011/0284582 A1 Nov. 24, 2011

Related U.S. Application Data

(60) Provisional application No. 61/022,859, filed on Jan. 23, 2008.

(51) Int. Cl.
*B67D 7/74* (2010.01)
*A61C 5/06* (2006.01)
(Continued)

(52) U.S. Cl.
CPC .................. *A61C 5/062* (2013.01); *A61C 3/005* (2013.01); *B65D 81/3261* (2013.01); *A61C 2202/01* (2013.01); *Y10T 29/494* (2015.01)

(58) Field of Classification Search
CPC ..... B65D 81/3261; A61C 3/005; A61C 5/062
USPC ............... 222/94, 93, 97, 106, 107, 574, 129; 29/890.09; 206/469, 470, 532
See application file for complete search history.

(56) References Cited

U.S. PATENT DOCUMENTS 2,898,744 A   8/1959   Robbins
3,336,669 A   8/1967   Kramer
(Continued)

FOREIGN PATENT DOCUMENTS

DE    37 17 512    12/1987
DE    100 09 622   3/2000
(Continued)

OTHER PUBLICATIONS

Adper™ Prompt™ L-Pop™ Self-Etch Adhesive Now with Easier Activation and Iprovied Chemistry for Higher Performance, pp. 1-4, ESPE, 70-20069-3435-7, Copyright 2002.
(Continued)

*Primary Examiner* — Paul R Durand
*Assistant Examiner* — Donnell Long (57) ABSTRACT

The present invention is related to a device for providing a dental material. The device has first and second compartments formed between sheet-like layers, and first and second dispensing outlets for the first and second compartments, respectively. For use, the device can be positioned with the compartments overlapping each other and with the dispensing outlets located side by side. The invention may provide a rather inexpensive device which may help a user in a convenient preparation of a dental material.

13 Claims, 8 Drawing Sheets

(51) Int. Cl.
*A61C 3/00* (2006.01)
*B65D 81/32* (2006.01)

(56) References Cited

U.S. PATENT DOCUMENTS

| | | | | |
|---|---|---|---|---|
| 3,421,661 | A | * | 1/1969 | Price .................. 222/94 |
| 3,521,805 | A | * | 7/1970 | Ward .................. 206/539 |
| 3,618,751 | A | | 11/1971 | Rich |
| 3,659,706 | A | | 5/1972 | Serrell |
| 3,756,389 | A | | 9/1973 | Firth |
| 3,862,684 | A | * | 1/1975 | Schmitt .............. 206/277 |
| 4,140,409 | A | * | 2/1979 | DeVries .............. 401/132 |
| 4,519,499 | A | | 5/1985 | Stone et al. |
| 4,790,429 | A | * | 12/1988 | Fukushima ........ 206/219 |
| 4,880,111 | A | | 11/1989 | Bagwell et al. |
| 4,911,304 | A | | 3/1990 | Bunin |
| 4,952,068 | A | | 8/1990 | Flint |
| 5,001,880 | A | | 3/1991 | Smith |
| 5,549,204 | A | | 8/1996 | Toren |
| 5,558,874 | A | * | 9/1996 | Haber et al. ......... 424/402 |
| 5,954,996 | A | | 9/1999 | Discko, Jr. |
| 6,105,761 | A | * | 8/2000 | Peuker et al. ........ 206/229 |
| 6,328,159 | B1 | | 12/2001 | Discko, Jr. |
| 6,612,769 | B2 | | 9/2003 | Lee et al. |
| 6,634,498 | B2 | | 10/2003 | Kayerød et al. |
| 6,695,515 | B1 | | 2/2004 | Fleury |
| 6,779,657 | B2 | | 8/2004 | Mainwaring et al. |
| 7,086,528 | B2 | * | 8/2006 | Raia et al. ........... 206/229 |
| 7,243,789 | B2 | | 7/2007 | Discko, Jr. |
| 7,320,398 | B2 | * | 1/2008 | Bertl et al. .......... 206/229 |
| 7,325,703 | B2 | * | 2/2008 | Gherdan et al. ..... 222/94 |
| 7,374,040 | B2 | | 5/2008 | Lee et al. |
| 2003/0019883 | A1 | | 1/2003 | De Laforcade |
| 2003/0038040 | A1 | | 2/2003 | Bertl et al. |
| 2003/0146117 | A1 | | 8/2003 | Raja et al. |
| 2004/0065679 | A1 | | 4/2004 | Peuker |
| 2005/0150904 | A1 | | 7/2005 | Suchan et al. |
| 2006/0118434 | A1 | | 6/2006 | Leiner et al. |
| 2006/0131189 | A1 | | 6/2006 | Lee et al. |
| 2006/0283761 | A1 | * | 12/2006 | Gherdan et al. ..... 206/532 |
| 2008/0171164 | A1 | | 7/2008 | Lee et al. |
| 2010/0065582 | A1 | * | 3/2010 | Nelson et al. ....... 222/107 |

FOREIGN PATENT DOCUMENTS

| | | | |
|---|---|---|---|
| WO | WO 00/73146 | | 12/2000 |
| WO | WO 02/064444 | | 8/2002 |
| WO | WO 2004/041107 | A | 5/2004 |
| WO | WO 2005/087614 | | 9/2005 |
| WO | WO 2005087614 | A1 * | 9/2005 |

OTHER PUBLICATIONS

U.S. Appl. No. 12/052,017, entitled "Devices for Storing and Dispensing Compositions," filed Mar. 20, 2008.

U.S. Appl. No. 61/022,859, entitled "Dental Package, and Method of Making the Package," filed Jan. 23, 2008.

International Search Report for International Publication No. PCT/US2009/031432, dated Feb. 14, 2011.

* cited by examiner

DENTAL PACKAGE, AND METHOD OF MAKING THE PACKAGE

CROSS REFERENCE TO RELATED APPLICATIONS

This application is a national stage filing under 35 U.S.C. 371 of PCT/US2009/031432, filed Jan. 20, 2009, which claims priority to U.S. Patent Application No. 61/022,859, filed Jan. 23, 2008, the disclosure of which is incorporated by reference in its/their entirety herein.

The present invention relates to a device for providing a multi-component dental material. In particular, the present invention relates to a device and a kit that allow storing the dental material in the device, and dispensing the components of the dental material to a desired location. The invention further relates to a method of providing a dental material from such a device or kit.

BACKGROUND OF THE INVENTION

In the dental field a number of liquid and semi-liquid compositions are made from two or more flowable components that are typically separately stored, and only mixed together immediately prior to use. For example, certain dental compositions like dental adhesives, sealants or etchings are offered in packages that initially store components of the dental composition separate from one another. The dental compositions then can be obtained by mixing the components at the time, and in the amount needed. After mixing the components, the dental composition may be applied to a desired place, for example in the cavity of a tooth in a patient's mouth.

A variety of packages have been proposed over the years for separately containing and storing components of multi-component compositions. Examples of commonly-used packages for multi-component compositions include dual-chamber cartridges, dual-chamber syringes or dual-chamber blister packages. Such packages are typically designed to provide a readily mixable composition, or to provide the components individually for subsequent mixing. There are also single use packages for providing suitable amounts of composition for a single treatment.

For example U.S. Pat. No. 6,105,761 discloses a device for storing and dispensing preferably flowable substances. The device preferably includes a container formed by two sheets that are interconnected by heat sealing. The sheets preferably form a compartment for receiving a component, which may be a liquid, and a pocket for receiving a brush. In the area between the compartment and the pocket, the connection between the sheets includes a pre-defined break zone which can be released by pressure exerted on the compartment, to force the liquid from the compartment into the pocket and wet the tip of the brush disposed therein.

DE 100 09 622 discloses a device for storing and dispensing preferably flowable substances. The device preferably includes a container formed by two sheets, interconnected by heat sealing and cooperating to form a compartment for receiving a substance and a pocket for receiving a brush. The device is preferably designed to allow the substance stored in the compartment to be forced in a pocket and from there onto a film sheet where it can be mixed.

US 2006/0131189 discloses a packaging article having chambers preferably defined by sealed connections between films. The device may have one or more receiving chambers which can receive the components that may be stored in the chambers. The receiving chambers are preferably accessible through passageways that extend from the exterior of the device into the receiving chambers. Brushes may be pushed through the passageways for picking up components from the receiving chambers.

There is still a desire for packages that can be used to provide multi-component compositions for different applications. In particular, suitable packages for providing relatively small amounts of a composition are desirable. Moreover, there is a need for packages that can be used in health care fields such as in dentistry, with its associated hygiene requirements. There is also a general need for packages that are relatively inexpensive to manufacture and use.

SUMMARY OF THE INVENTION

A first aspect of the invention is related to a device for providing a dental material, comprising:
  a first and a second compartment formed between interconnected sheet-like layers,
  a first and a second dispensing outlet for the first and second compartments, respectively, and
  a seal separating one of the outlets from the corresponding compartment,
  the seal being formed by the layers in an area in which the layers are interconnected but adapted to separate upon forcing a component of the dental material between the layers,
  wherein the device is adapted such that for dispensing of the dental material the dispensing outlets can be positioned side by side, and the compartments can be positioned to at least partially overlap each other.

The invention may be advantageous for providing two- or multi-component materials in single-use quantities. The invention may also provide a package that is convenient to use, which may be relatively inexpensive. It may be advantageous to design the package so that the components can be dispensed adjacent to one another without bringing them in contact with one another. Further, the invention may be useful for users that prefer materials mixed by hand over those automatically mixed, for example by static or dynamic mixing devices. The invention may also allow each user to select the mixing ratios of the two- or multi-component materials, by dispensing more or less of one or both components. Further, with the invention a package may be provided which allows storage of the material over a relatively long time, and supports convenient hand mixing. The invention may also be advantageous in that it enables a user to assess the quantities (and thus the ratio) of material components prior to mixing. Another advantage may be provided by the invention in that it allows to dispense multi-component material that are not intended or suitable to be mixed with each other, however used separately. This may be useful, for example, if different components are layered (for example at predetermined quantities) on a surface, like a primer and an adhesive.

Preferably the first and second compartments are formed between unconnected areas of the interconnected sheet-like layers. Therefore the unconnected areas of the interconnected layers preferably at least partially overlap each other when the compartments are positioned to at least partially overlap each other.

The interconnection between the sheet-like layers is preferably an interconnection between a major surface of one layer and a major surface of another layer. The sheet-like layers are preferably separate sheets. Alternatively, the sheet-like layers may be part of one larger sheet that is folded to form the individual layers.

In one embodiment the first and the second compartments are formed by a first and a second sheet-like layer that are interconnected. The first and second sheet-like layers are preferably two separate sheets. Alternatively, the first and second sheet-like layers may be part of one larger sheet that is folded to form the first and second layers.

In another embodiment of the invention the first dispensing outlet is associated with a first seal sealing the first compartment, and the second dispensing outlet is associated with a second seal sealing the second compartment. Preferably the device comprises a seal between at least one of the dispensing outlets and the corresponding compartment. In particular, preferably the device comprises a first seal between the first dispensing outlet and the first compartment, and a second seal between the second dispensing outlet and the second compartment.

The first dispensing outlet and the first compartment may be connected by a first passageway which is openably closed by the first seal. In one embodiment the passageway and the outlet may not be distinct parts, but the outlet may itself form the passageway which is openably closed. This may be achieved, for example, in that the layers are connected at an edge only rather than over a surface. Further, the second dispensing outlet and the second compartment may be connected by a second passageway which is openably closed by the second seal. Preferably, the passageways have a relatively small capacity for holding or retaining material dispensed through them. Therefore the amount of material that may reside in the passageways after dispensation may be minimized. Preferably the volume capacity of passageway is smaller than the capacity of any of the compartments of the device. Preferably the passageways do not form a chamber to buffer material from which material may be picked up.

The device of the invention is preferably adapted to be brought (for example folded) into a shape in which the compartments at least partially overlap each another, and in which the dispensing outlets are located side by side. Preferably the device is adapted to be bought in such shape for dispensing of the dental material. An embodiment in which dispensing outlets are located side by side may comprise openings that face in the same (or generally the same) direction. The openings may also be arranged generally in a common plane. Further, an embodiment in which dispensing outlets are located side by side may comprise parallel (or generally parallel) extending passageways.

The device of the invention preferably further comprises a predetermined fold line, or a line of weakness. Therefore the device may be foldable along the predetermined fold line for positioning the outlets and the compartments. For predetermination of the fold line the device may comprise at least one of a perforation or set of perforations, a thinned portion, at least one generally V-shaped recess, and a living hinge. The perforation may for example comprise a hole or slit, or several holes or slits extending through at least one, or all of the layers of the device. The perforation may extend linearly on non-linearly, for example arced, which may help folded parts to be retained in the folded position. Such hole preferably extends between the major surfaces of the layer(s). The V-shaped recess preferably also extends between the major surfaces of the layer(s). The thinned portion may be an indentation in at least one of the layers. The thinned portion therefore preferably locally reduces the thickness (dimension between the major surfaces of the layer(s)) of the layer.

The predetermination of the fold line may be generally achieved by locally reducing the flexural stiffness of the device. Thus, the application of bending forces to the device preferably causes bending in the region of reduced flexural stiffness.

In a further embodiment the predetermined fold line is aligned with the axis of symmetry of at least two items of the device, preferably of two edges of the device. The predetermined fold line may also be aligned with the axis of symmetry of the general shape of the device. The predetermined fold line may also be generally aligned with the axis of symmetry between two juxtaposed outlets and between two juxtaposed compartments. Thereby the device may be adapted such that the dispensing outlets can be positioned side by side for dispensing of the dental material, and such that the compartments can be positioned to at least partially overlap each another.

In another embodiment the device has at least a third compartment. The third compartment may be connectable (brought into fluid communication) to the first or the second compartment. Therefore a passageway may extend between the third compartment and the first compartment, or between the third compartment and the second compartment. The passageway may comprise an openable seal being preferably formed by the layers in an area in which the layers are interconnected but adapted to separate upon forcing a component of the dental material between the layers. Furthermore the device may have two, three, four or more compartments.

In another embodiment the device further comprises a mixing surface on which the dental material can be mixed. The mixing surface may be provided by or on one of the sheet-like layers. For example, one of the layers may project beyond the other layer(s), and the projecting portion may provide or form the mixing surface. The mixing surface may, however, also overlap with at least one of the compartments of the device. The mixing surface may in particular also overlap at least partially with an unconnected area between which a compartment of the device is formed. For example, one of the layers may with one major surface form part of the compartment(s) and the opposite major surface may form the mixing surface. The mixing surface is preferably generally arranged adjacent the outlets of the device. Therefore material components dispensed from the device may land on the mixing surface without touching each other. Because of the arrangement of the mixing surface adjacent the outlets of the device the materials may adhere to the mixing surface independently from the orientation of the device (for example with the outlets facing up, down, or in a horizontal direction). Such adhesion may be caused due to natural surface energy interaction between the material component and the mixing surface.

Another aspect of the invention is directed to a method of making a device of the invention. The method comprises the steps of:
providing a first layer;
providing a component on the first layer;
interconnecting a second layer and the first layer and thereby define a compartment which contains the component. The method may further comprise the step of predetermining a fold line at the device, by at least one of
perforating a layer of the device;
notching a layer of the device; and
recessing at least one layer of the device.

The method may also comprise the step of printing a pattern which optically indicates the fold line. In another embodiment the method further comprises the step of including a hole or a slit in a layer of the device. Preferably the hole or slit forms an opening which is located adjacent a dispensing outlet of the device.

Still another aspect of the invention is directed to a method for preparing a dental material. The method comprises the steps of:
  providing a device according to the invention; and
  dispensing two components next to one another, but not touching each other.

The two components may be dispensed generally simultaneously. Further, the two components may be dispensed without substantially repositioning the device between dispensing the individual components.

In an embodiment the method also comprises mixing of at least a portion of the materials dispensed.

Another aspect of the invention is related to a kit, comprising a device of the invention, and an applicator. The kit may further comprise a mixing pad, instructions for use of the device, and/or another package comprising a dental material.

Still another aspect of the invention relates to a device having a compartment formed between interconnected sheet-like layers. The device preferably has a seal which is formed by the layers in the area in which the layers are interconnected. The area forming the seal is preferably adapted to separate upon forcing the material between the layers. The seal also preferably separates the compartment from a corresponding outlet.

Preferably the device has a first and a second layer forming the compartment, wherein the first and second layers in a first condition are shaped to form the compartment for receiving a component of a dental material. At least one of the first and the second layers is adapted to be deformed towards a second condition in which a surface of the first layer and a surface of the second layer generally conform in shape with one another. In the second condition the compartment is preferably reduced in volume or capacity relative to the first condition. The first and second layers in the first condition are preferably shaped so that facing surfaces of the first and second layers are different in shape. Further in the second condition the first and second layers are shaped so that the shape of one layer is generally a proportional enlargement of the other layer.

In one embodiment the first layer in the first condition may be generally dome shaped and the second layer may have an annular bulge. The outer diameter of the annular bulge may generally correspond to the outer diameter of the dome. The annular bulge may be arranged concentrically with the dome. Further the annular bulge with its bulged area preferably projects into the inner side of the dome. The dome may have an outer diameter of between about 5 mm and about 30 mm, and an inner height of between about 1 mm and about 6 mm. The annular bulge may have an outer diameter of between about 5 mm and about 30 mm, and an outer height (protrusion from flat layer) of between about 0.5 mm and about 3 mm. The annular bulge may further have a width (outer diameter–inner diameter) of between about 1 mm and about 3 mm.

The capacity of the compartment may be between about 10 µl and about 2200 µl Such a device may help to minimize residual material in the device after use.

DETAILED DESCRIPTION OF THE FIGURES

Figure 1:
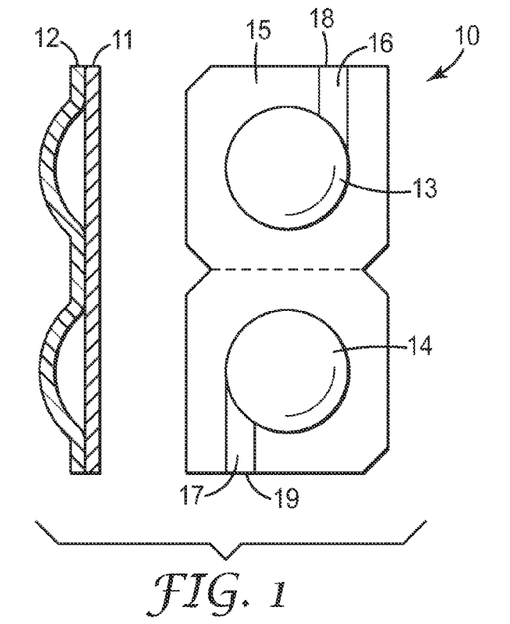
FIG. 1 is a cross-sectional side view and a top view of a device according to an embodiment of the invention.

FIG. 1 shows a top and a cross-sectional side view of the device 10 according to one embodiment of the invention. The device 10 has two compartments 13, 14 for containing components of a material. The compartments 13, 14 are formed between layers 11, 12 that are interconnected in the (preferably permanent) interconnection area 15. The compartments 13, 14 have dispensing outlets 18, 19 respectively. In this example, passage areas 16, 17 are arranged between the dispensing outlets 18, 19 and the compartments 13, 14. The layers 11, 12 are (preferably non-permanently) interconnected in at least a part of the passage areas 16, 17 to form openable seals for each of the compartments 13, 14. Preferably the layers 11, 12 are interconnected non-permanently in generally the entire passage areas 16, 17. The non-permanent interconnection of the layers in the passage areas is preferably of a lower bond strength than the permanent interconnection of the layers in the interconnection area 15. Therefore when a dispensing pressure is applied on a compartment, for example, it forces open the non-permanent interconnections in the passage areas, but not the permanent interconnections. Thereby the material is also enabled to flow through the passage areas toward the corresponding openings. Preferably the openable seals are adapted to open due to pressurizing the components by applying finger pressure to the compartments. Finger pressure is preferably in a range of 5 N to 70 N, preferably in a range of 15 N to 50 N. The openable seal and the permanent interconnection 15, in combination, preferably provide a hermetic seal for the compartments 13, 14. The openable seal further preferably allows the compartment 13, 14 to be opened for use of the device. Components stored in the compartments 13, 14 may thus be dispensed from the device 10 through the outlets 18, 19.

The layers may generally be interconnected by heat sealing. Different bond strengths for the interconnection between the layers may be achieved by using different temperatures and/or different sealing durations.

The device 10, as illustrated in the cross-sectional side view, may comprise a larger top layer 12 and a larger bottom layer 11 forming both compartments 13, 14. However, a larger bottom layer may also be used in combination with individual top layers for forming the compartments 13, 14. Alternatively a larger top layer may be used in combination with individual bottom layers to form the compartments. In another alternative embodiment the compartments may also each be formed individually by separate top and bottom layers, and the partial devices so formed may be interconnected to form the device according to the invention.

The layers may be bulged out to provide a certain volume for the compartments, as shown at layer 12 in FIG. 1. Such bulges further may facilitate filling. For example, the bulges of layer 12 may be filled with components prior to interconnecting the layer 12 with the layer 11. The bulges may in addition or instead be arranged in layer 11.

The compartments of the device may have a capacity to store quantities of between about 0.01 ml and about 3 ml. Therefore the device may be suitable for providing material in the rather small quantities typically used in dentistry. Preferably the individual compartments of the device have a capacity to provide a total quantity of material sufficient for a single dental treatment. Such total quantity may be between about 0.03 ml and about 1.5 ml. The mixing ratio may for example be 1:1 or 2:1 for example, but may generally be selected at values between, or beyond as appropriate.

Figure 2A:
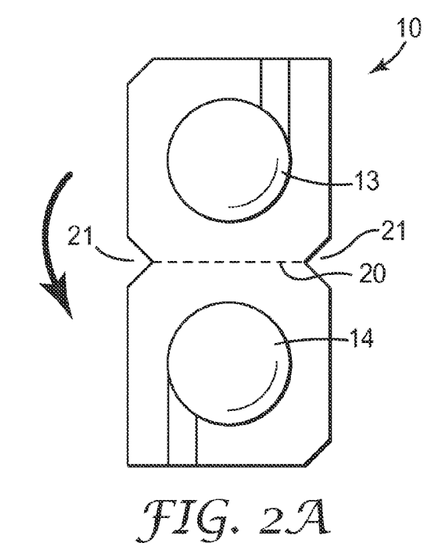
FIGS. 2A, 2B are top views of an unfolded (FIG. 2A) and a folded (FIG. 2B) device according to embodiments of the invention.
Figure 2B:
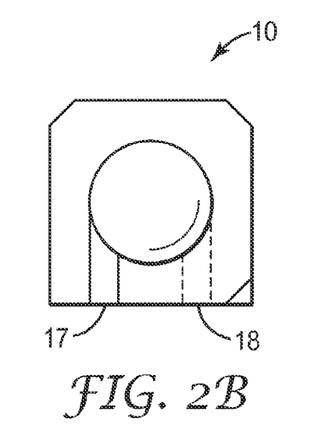

FIGS. 2A and 2B illustrate the preparation of the device for use. The device may be manufactured in a shape as shown in FIG. 2A. Such shape may, for example, be selected appropriately for manufacturing and filling. For use, the device may be folded along fold line 20 by about 180° as shown in FIG. 2B. The device 10 of the example has indentations 21 to provide for a generally coincident overlap of the folded portions. The fold line may additionally or alternatively be perforated or notched. A similar configuration as shown in FIG. 2B may be provided by arranging two separate partial devices, each having only one compartment, on top of each other to form the device according to the invention. In the configuration shown in FIG. 2B the compartments overlap each other. In particular the unconnected areas of the interconnected layers overlap each other. This allows a user to compress the compartments 13, 14 generally simultaneously between two fingers for dispensing the components from both compartments. The outlets of the device are arranged side by side. Therefore, the device is configured so that the components that may be stored in the compartments can be dispensed without bringing them in contact to one another. Preferably the dispensing outlets are spaced from one another. In more particular, the dispensing outlets are spaced from one another (shortest edge to edge measurement) by between about 5 mm to 20 mm, preferably spaced by about 7.5 mm. This allows for dispensation of the components that may be stored in the compartments to a desired place spaced apart from one another. If for example a user dispenses such components on a mixing pad the components may not touch each other initially. This may for example be advantageous for the use of components which chemically interact, for example harden, when mixed. A user could therefore prepare the required components, for example, on a mixing pad and only mix small portions of the components as required. In this case the individual components may be kept on the pad over a relatively long time, and smaller mixed portions that, for example, may generally rapidly harden may be easily obtained as required.

Figure 3:
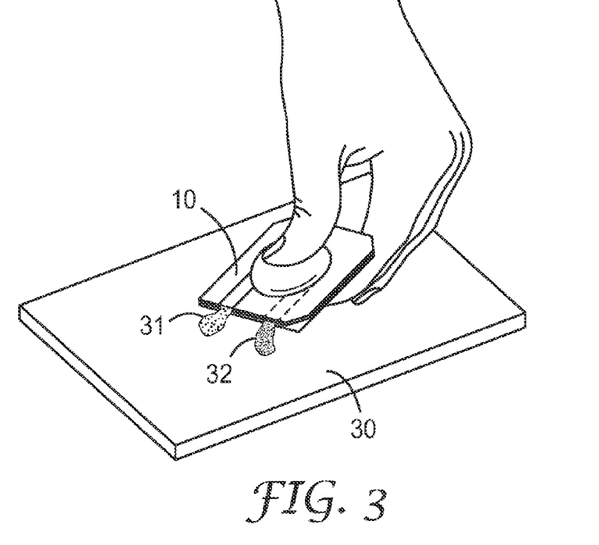
FIG. 3 is a perspective view of a device in use, according to an embodiment of the invention.

FIG. 3 illustrates the device according to the invention in an exemplary use. The device 10 is shown in a condition where the openable seals are opened and some of the components 31, 32 are dispensed on a pad 30. This can be achieved, for example, if the user exerts finger pressure on the compartments until the seals open. The components 31, 32 are spaced from each other on the pad so that they do not touch. A user can assess the quantities of the dispensed components and therefore may check the approximate mixing ratio of the components prior to mixing.

Figure 4A:
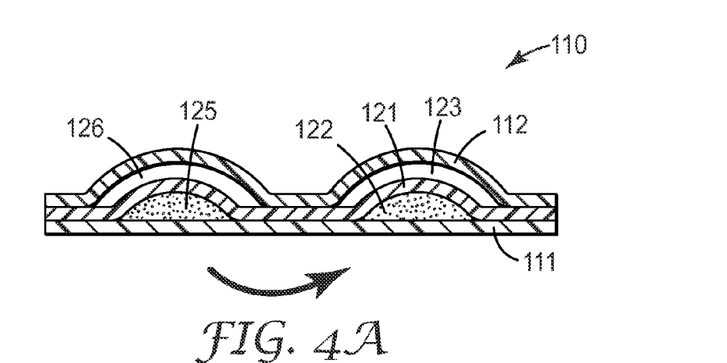
FIGS. 4A, 4B, 4C are views of a device according to an alternative embodiment of the invention.
Figure 4B:
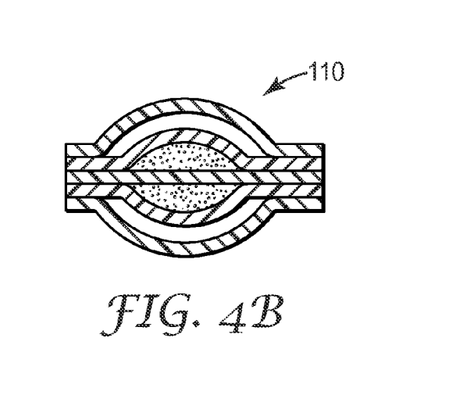
Figure 4C:
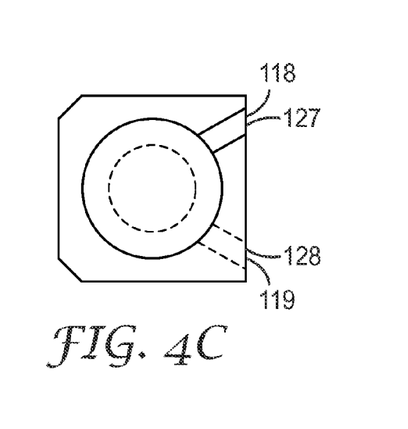

FIGS. 4A, 4B and 4C show an alternative embodiment of the invention. The device 110 has a bottom layer 111, a top layer 112, and an intermediate layer 121. The bottom layer 111 and the intermediate layer 121 form compartments 122, 125. Further, the top layer 112 together with intermediate layer 121 form compartments 123, 126. As shown in FIG. 4A the compartments 122, 125 are arranged within the compartments 123, 126. The configuration shown allows for dispensing more than two components with one device. The device 110 has preferably four dispensing outlets 118, 119, 127, 128. Preferably the four dispensing outlets are arranged in pairs of two dispensing outlets. For example, the dispensing outlets 118 and 127 may be arranged adjacent one another, and dispensing outlets 119 and 128 may be arranged adjacent one another. Further the pairs of dispensing outlets 118/127 and 119/128 are preferably arranged side by side, in particular preferably spaced from one another. Although the device is shown with four compartments 122, 123, 125, 126, another device may have only three compartments. For example the alternative device may only have one bulge in the intermediate layer 121 for forming the compartment 122 or the compartment 125. The device according to FIGS. 4A-4C may, for example, be advantageous for use with two chemically interacting components and a third component for coloring. In this case the chemically interacting components may be accommodated in nested compartments (for example in compartments 125, 126) that have adjacent dispensing outlets. Therefore the components contact each other as soon as they are dispensed from the device and may be easily mixed together. A third component containing a colorant, for example may be dispensed through another dispensing outlet remote from the chemically interacting components. Therefore a user can determine the amount of colorant, for example, for mixing with the chemically interacting components as desired for a certain application. A dentist may for example use the device for dispensing a hardenable two-component dental filling material that may be colored by a third component to match a color of a tooth or teeth in a patient's mouth.

Figure 5A:
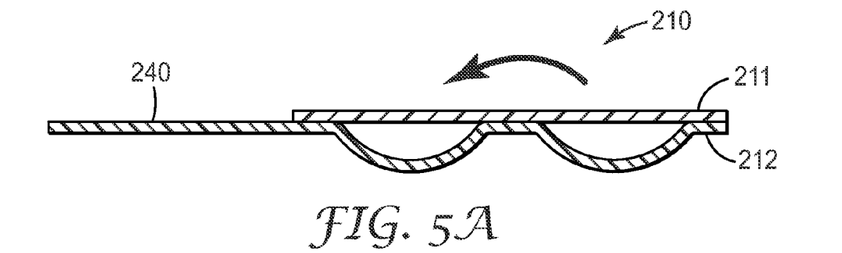
FIGS. 5A, 5B, 5C are views of a device comprising a mixing pad, according to an embodiment of the invention.
Figure 5B:
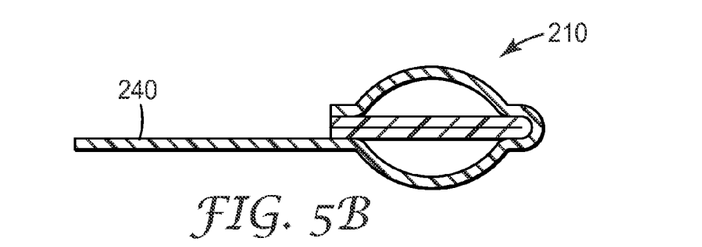
Figure 5C:
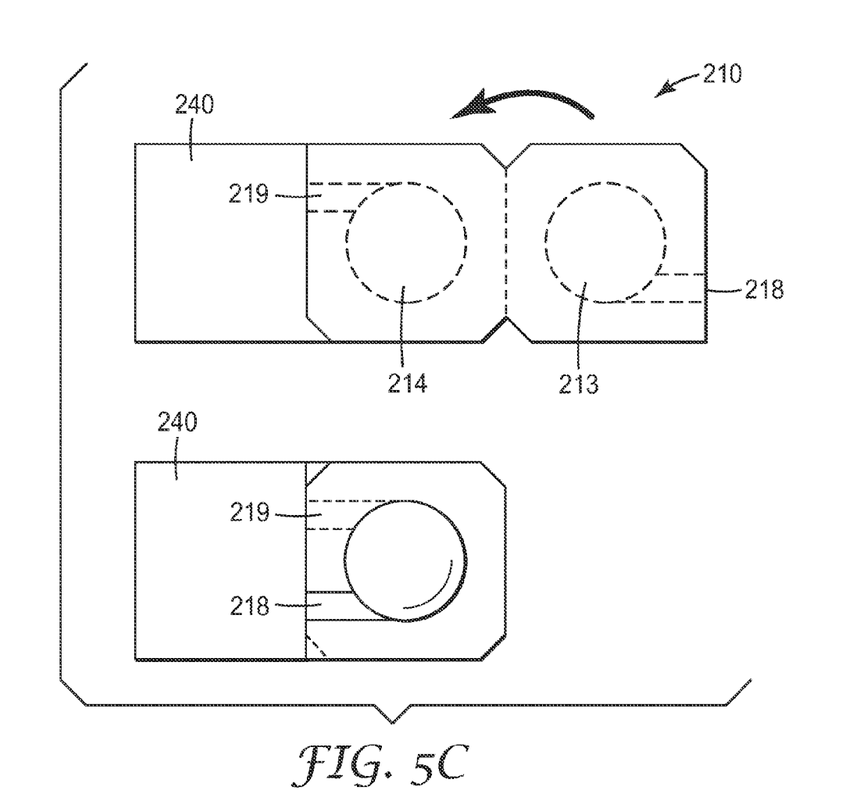

FIGS. 5A, 5B, and 5C show another embodiment of the invention. The device 210 generally corresponds to the device 10 of FIG. 1, and alternatively may be generally configured according to the device 110 as shown in FIGS. 4A-4C. However, the device 210 has a mixing pad 240 attached, which is located adjacent the dispensing outlets 219, 218 when the device is prepared for use (for example as shown in the lower illustration of FIG. 5C). The pad 240 may be part of the top layer 212, or part of the bottom layer 211, or a separate layer interconnected to the device. For example a separate layer forming the pad may be attached to the device by heat sealing or by use of an adhesive. The device 210 allows for receiving components that may be stored in the compartments 213, 214 on the pad 240. The components may be directly mixed on the pad 240 of the device. Therefore the mixing pad is made available for a user along with the device which facilitates the use of the device. Optionally any of the embodiments described herein may be furnished with an applicator, like a spatula or brush, so that all necessary items for use of the device may be provided together.

Figure 6A:
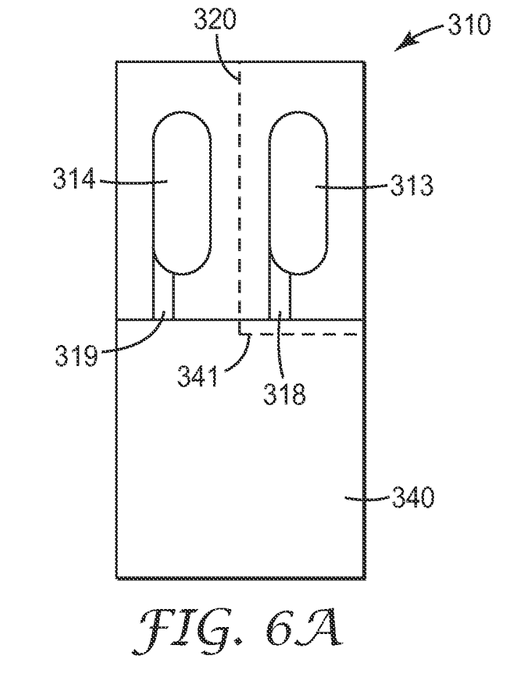
FIGS. 6A, 6B, 6C are views of an alternative device comprising a mixing pad, according to an embodiment of the invention.
Figure 6B:
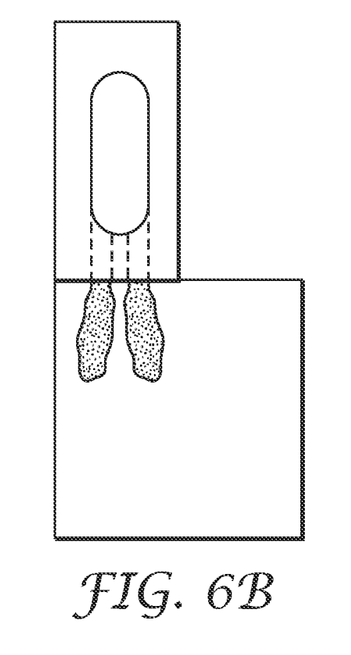
Figure 6C:
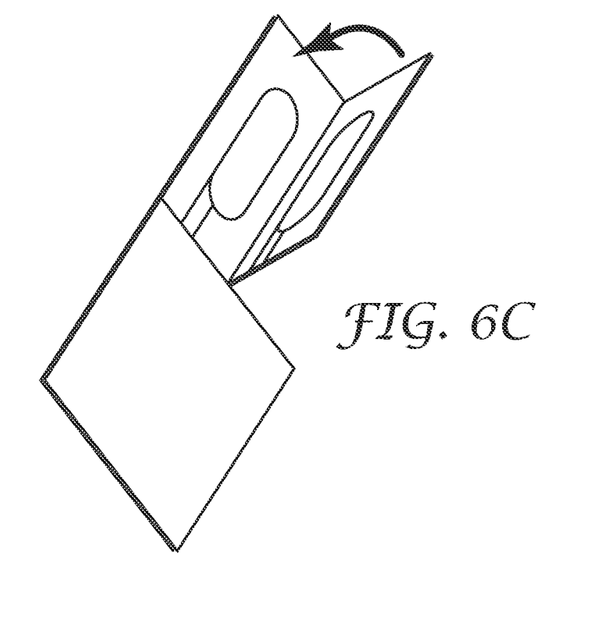

FIGS. 6A, 6B and 6C show another embodiment of the invention. The device 310 has two side by side compartments 313, 314 and corresponding dispensing outlets 318, 319. The device further has a pad 340 adjacent the dispensing outlets 318, 319. A perforation or area of weakness 320, 341 may be arranged in the device to allow the compartments 313, 314 to be folded on top of one another as shown in FIGS. 6B and 6C. Thereby the device 310 may be partially separated along the perforation or area of weakness 341. The arrangement of the compartments in this embodiment may be advantageous in that a relatively large mixing pad 340 can be provided quite easily.

Figure 7A:
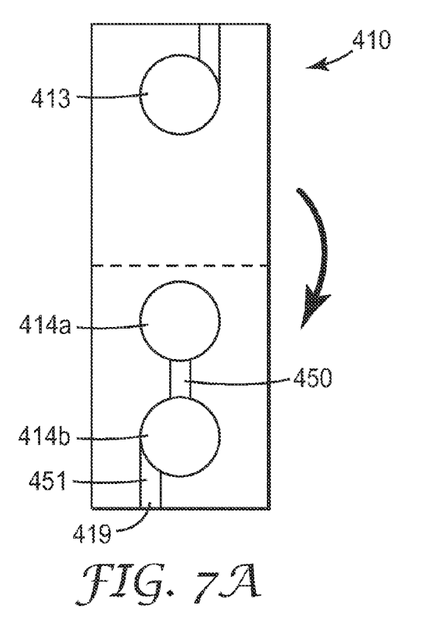
FIGS. 7A, 7B are top views of an unfolded (FIG. 7A) and folded (FIG. 7B) device according to embodiments of the invention.
Figure 7B:
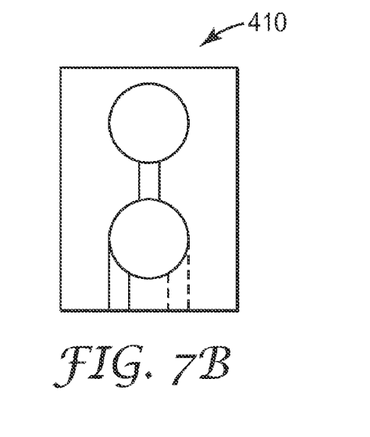

FIG. 7A shows an embodiment of the invention in which the device 410 has a compartment 413 and two compartments 414a, 414b. The compartments 414a and 414b are connectable to each other by a passageway between compartments 414a and 414b which is initially closed by an openable seal 450. The compartment 414b has a dispensing outlet 419, and an openable seal 451 is arranged between the dispensing outlet 419 and the compartment 414b. Therefore components in the compartments 414a and 414b are encapsulated in the device and kept separate from each other during storage of the device. For use the compartment 414a may be compressed so that the components stored in compartment 414a are pressurized and cause the openable seal 450 to open. At this stage the compartments 414a and 414b are in fluid communication with one another, and the openable seal 451 (toward the exterior of the device) is still closed. The components stored in compartment 414a may then be forced into compartment 414b by further compressing the compartment 414a. The components together may be moved between the compartments 414a, 414b to agitate them for mixing. This may be done by alternately compressing the compartments 414a and 414b. The mixture of the components of compartments 414a and 414b may be dispensed from the device along with the components of the compartment 413 when the device is folded as indicated in FIG. 7B and all compartments 413, 414a, and 414b are compressed generally simultaneously. The compartments that are connectable with one or more further compartments may generally be dimensioned to receive the total amount of all components that are stored in the connectable compartments. For example, the compartment 414b may be sized to receive the components of compartments 414b and the compartment 414a. Further, also the compartment 414a may be sized to receive the components of both compartments 414a and 414b.

Figure 8:
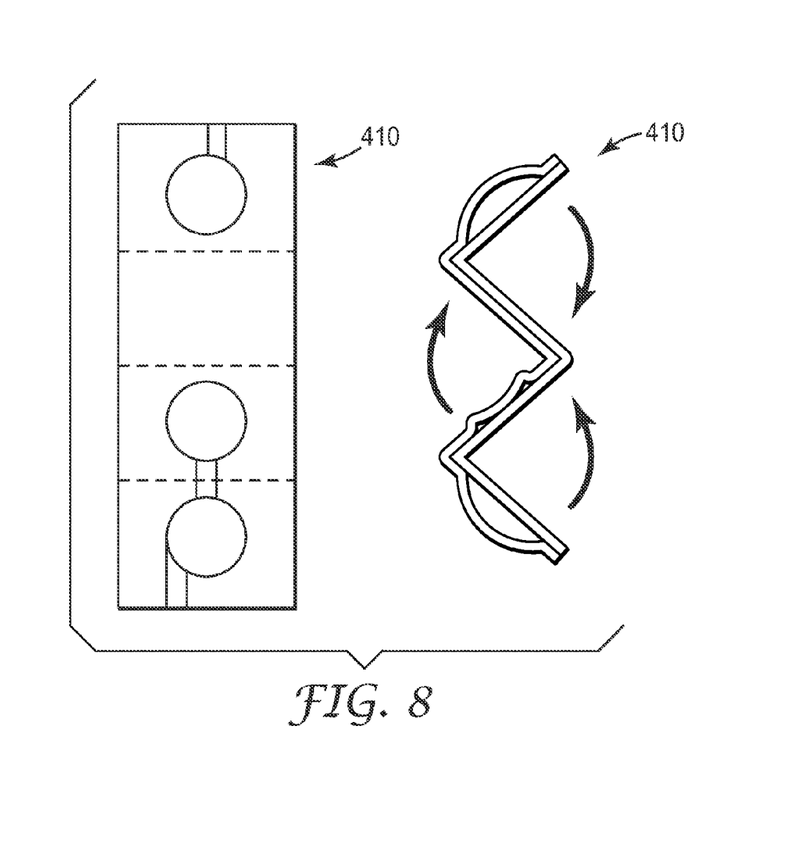
FIG. 8 is a top view and a side view of a device having alternative fold lines, according to an embodiment of the invention.

To prevent the mixture from flowing back toward compartment 414a while the device is used for dispensing, the device may be folded as indicated in FIG. 8.

Figure 9:
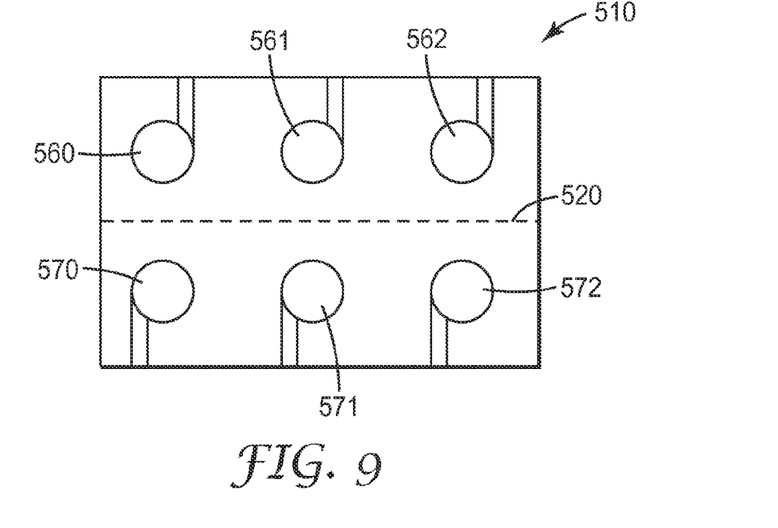
FIG. 9 is a top view of a device having a plurality of compartments, according to an embodiment of the invention.

FIG. 9 shows an embodiment of the invention in which the device has a plurality of compartments 560, 561, 562 and 570, 571, 572. The device 510 is foldable at fold line 520 so that the compartments 560, 561, 562 are positioned to overlap with compartments 570, 571, 572. Such an arrangement may be useful to provide different amounts of material as they may be required for different applications. This may make the device useful for the dispensation of different amounts of material.

FIG. 10 shows a device 610 according to an embodiment of the invention having compartments 613 and 614 which preferably are formed by substantially flat layers (indicated as 611, 612a and 612b). In this regard the term "substantially flat" means that preferably the layers are not permanently bulged or deformed prior to filling of the device, but compartments for holding material components are only provided by the flexibility or extensibility of the layers. The substantially flat layers of the device 610 comprise a bottom layer 611 on which top layers 612a, 612b are arranged (see also FIG. 10D). The top layers 612a, 612b are interconnected in permanent interconnection areas 615a, 615b to respectively form compartments 613, 614. The device 610 further has dispensing outlets 618, 619 and openable seals arranged between the dispensing outlets 618, 619 and the compartments 613, 614 respectively. In this embodiment the outlets are arranged within the base area of the device. This is in contrast to embodiments having dispensing outlets adjacent an edge of the device. As shown, however, the dispensing outlets are arranged adjacent the fold line 620 of the device 610. Therefore, for dispensing components from the device the device may be folded as shown in FIG. 10B so that the fold (at fold line 620) provides an edge of the device at which the dispensing outlets 618, 619 are arranged.

Figure 10A:
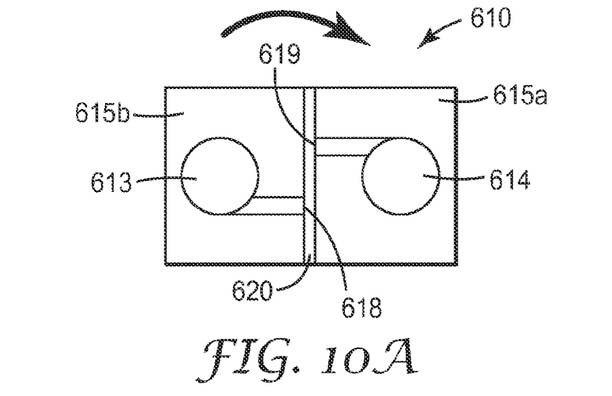
FIGS. 10A, 10B, 10C, 10D are views showing an alternative device providing a mixing surface on the device according to embodiments of the invention.
Figure 10B:
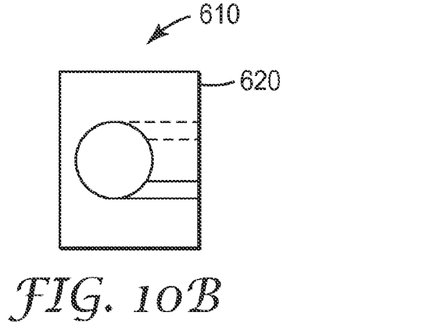
Figure 10C:
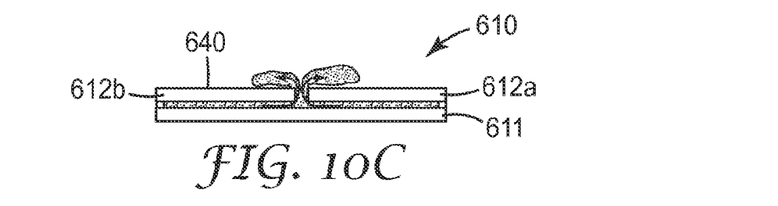
Figure 10D:
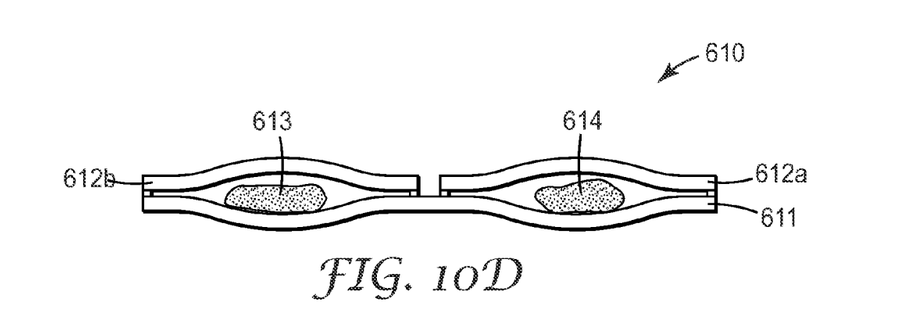

On the other hand the device 610 may be alternatively used without folding, as illustrated in FIG. 10C. The components of compartments 613 and 614 are dispensed through the outlets. This may be done, for example, by scraping a spatula over the compartments to cause the openable seals to open, and to force the components from the compartments 613, 614. Because the outlets are arranged within the base area of the device the components flow on top of the layers 612a and 612b. The top layers 612a and 612b may then be used as mixing surface 640. The spatula may for example also be used for mixing the components on the top layer of the device 610. Therefore the device itself can be used as a mixing surface 640. This may be advantageous in that the device 610 is flexible in use, for example, and may be used to dispense material at a desired place as illustrated in FIG. 10B, or it may be used as a mixing surface 640 as indicated in FIG. 10C. The device may therefore also help to save cost and waste because an additional mixing pad may not be required. The device 610 may also be convenient in use because an instrument, like a spatula, may be used to scrape over the device 610 to first cause the components to be dispensed from the compartments 613, 614 onto the top layers 612a, 612b of the device 610, and subsequently for mixing the dispensed components.

Figure 11:
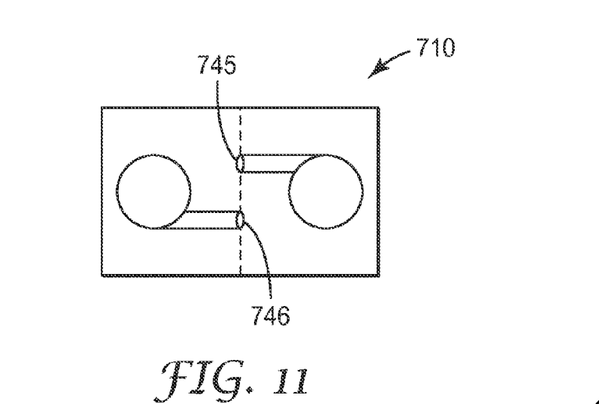
FIG. 11 is a top view of an alternative device of FIGS. 10A-10D.

FIG. 11 shows a variant of the device shown in FIGS. 10A-10D. Instead of two separate top layers the device 710 has a larger continuous top layer, but has openings 745, 746. The openings 745, 746 are located adjacent the dispensing outlets (not shown) of the device 710 so that material dispensed can flow from the dispensing outlets through the openings 745, 746. The device 710 may be used similarly to the device 610 including in a way indicated in FIG. 10B. However, because of the relatively large continuous top layer the device may in particular be advantageous for use as a mixing surface. The openings 745, 746 may be formed as generally circular or elliptical holes, or preferably as slits. Slits may generally provide for trapping only a low amount of material, and may therefore be particularly advantageous in combination with this embodiment.

Figure 12:
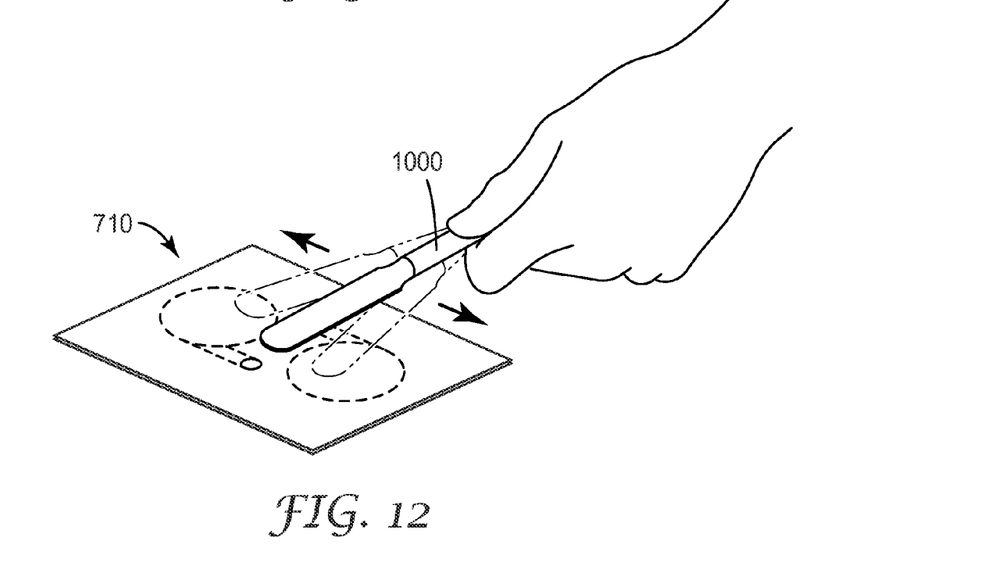
FIG. 12 is a perspective view of a device as illustrated in FIGS. 10A-10D, and FIG. 11.

The devices 610, 710 (or other embodiments in this specification providing a mixing surface) may have top layers that provide for easy mixing. For example the top layers may have a certain thickness, stiffness, and/or a certain surface quality. The top layers may for example comprise a paper substrate. The paper substrate may provide the stiffness required for mixing the components stored in the device. The paper may also be coated with a plastic layer which provides the mixing surface. The plastic layer may provide good sliding properties for the instruments used for mixing, and on the other hand may prevent components from penetrating into the paper structure. The plastic layer may provide also a relatively low surface energy so that the mixed material can be removed from the surface easily and almost completely. A use of the device 710 with a spatula 1000 is illustrated in FIG. 12.

The layers used to form embodiments of the invention may form a diffusion or permeation barrier between the compartment and the environment, for example to avoid the escape of ingredients of the component stored in the compartment through the layer by permeation. This may for example allow storing components including rather volatile ingredients (like some solvents) over a relatively long time period.

An exemplary first configuration of a layer as it may be used with the invention may be formed of a polypropylene sublayer, an aluminum sublayer, and a polyethylene sublayer. In particular an oriented polypropylene (OPP) sublayer, an aluminum sublayer, an ethylene acrylic acid (EAA) sublayer and a high-density polyethylene sublayer. An exemplary second configuration of a layer as it may be used with the invention may be formed of a polyethylene terephthalate sublayer, an aluminum sublayer, and a polyethylene sublayer. In particular a polyethylene terephthalate layer, an aluminum layer, an ethylene acrylic acid (EAA) sublayer, and a polyethylene sublayer. In both configurations, a polyethylene terephthalate sublayer may be provided between the aluminum sublayer and polyethylene layers.

Figure 13A:
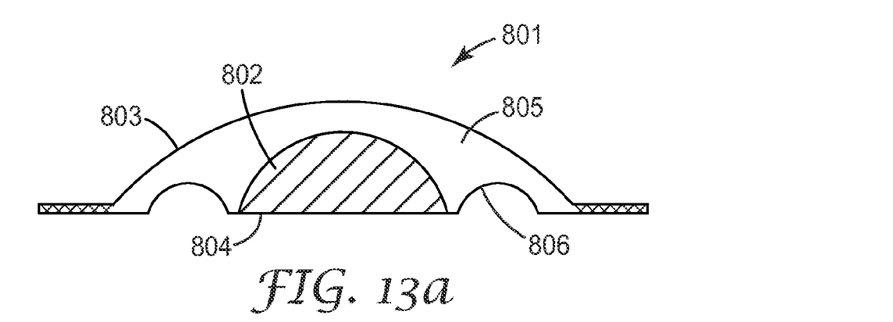
FIGS. 13a, 13b are cross-sectional views of a device according to the invention.
Figure 13B:
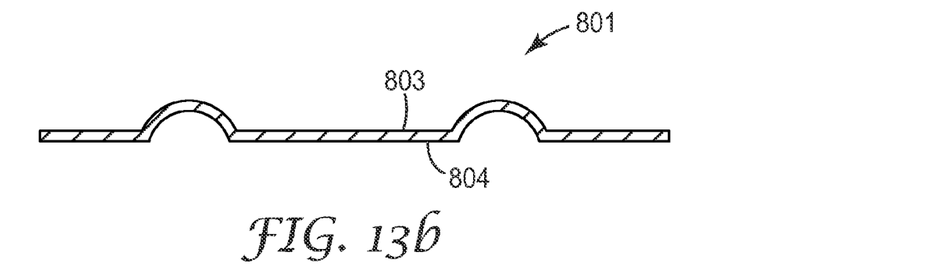

A portion of a device 801 according to the invention is shown in FIGS. 13a and 13b, with FIG. 13a illustrating the device in an initial state (when filled with an amount of material 802), and FIG. 13b illustrating the device when used (after the material has been dispensed from the device). The device 801 has a compartment 805 formed between interconnected sheet-like layers 803, 804. The device 801 further has a seal which is formed by the layers 803, 804 in the area in which the layers 803, 804 are interconnected. The area forming the seal is adapted to separate upon forcing the material 802 between the layers. The seal also preferably separates the compartment 805 from a corresponding outlet (not shown). Thus the material 802 is preferably initially tightly sealed in the compartment 805, but may be displaced from the compartment 805 through the seal towards the outlet by pressurizing the compartment 805. The device 801 has further a pre-deformed area 806 in layer 804 which in the example shown is an annular bulge. The compartment 805 is preferably formed by generally thin and deformable layers 803, 804, and the resulting shape of a deformation from pressurizing the compartment may not be predictable. However, it has been found that a pre-deformed area like the one shown in FIGS. 13a, 13b can help to minimize the residual volume of the compartment after it has been compressed. For example, the resulting shape after compression of the bulged out area of the layer 803 (in FIG. 13a the top layer of the device) generally conforms the layer 804 (in FIG. 13a the bottom layer of the device). Thus the resulting residual volume in the compartment, and also the residual amount of material after use of the device may be minimized. The skilled person may appreciate other shapes for the pre-deformed area in one or both of the layers and still achieve an equivalent or similar effect.

It is also pointed out that the embodiment shown in FIGS. 13a, 13b is not restricted to a combination with other features of the invention, but may be combined with other devices in which a compartment is compressed or deformed to dispense material from that compartment. Exemplary devices which may be used with the embodiment of FIGS. 13a, 13b are described in patent applications and/or patents EP 1830736, EP 1526092, EP 1644264, EP 1334047, DE 10047679, EP 1301788, EP 1286899, DE 10009629, EP 1259438, EP 1259440, DE 10009622, EP 1240087, EP 0895943. Features and embodiments of the devices described in these patent applications and/or patents may be combined with the embodiment shown in FIGS. 13a, 13b, and are for this purpose incorporated by reference herein.

EXAMPLES

Devices having a pre-deformed area according to the embodiment shown in FIGS. 13a, 13b (Example 1) were tested in comparison to equivalent devices without a pre-deformed area (Example 2). The devices each were prefilled with the same amount of material and assembled in an automatic filling machine. The prefilled devices were each weighed in their initial states. In Example 1 as well in Example 2 three different test persons each used 13 or 14 devices to dispense the material contained therein (41 sample in Example 1 and 40 samples in Example 2). The test persons were instructed to dispense the material from the devices by pressurizing the compartments between the thumb and the forefinger, and thereby to apply as much pressure as they can to dispense as much material as possible from the devices. After the material had been dispensed each device was weighed again. From the difference between the initial and remaining weight the material dispensed from the devices was calculated. Table 1 and 2 show the dispensed material of Example 1 and Example 2, respectively.

Figure 14:
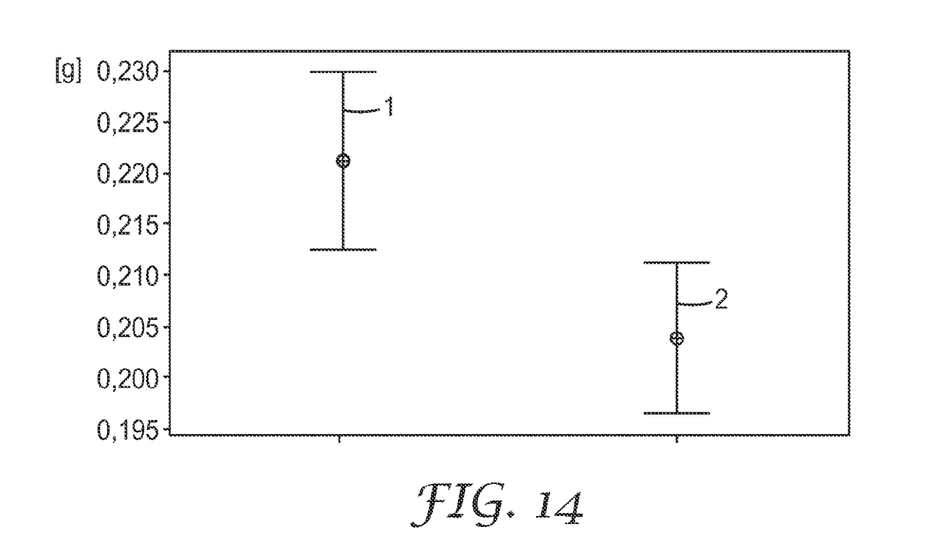
FIG. 14 is a diagram illustrating amounts of material that can be dispensed from a device according to the invention.

FIG. 14 shows a diagram showing the ranges of the amount of dispensed material in Example 1 (indicated by reference number 1) versus Example 2 (indicated by reference number 2). It can be seen that more material could be dispensed from the devices of Example 1 (having the annular bulge) relative to the devices of the Example 2 (having no annular bulge). This also indicates that less residual material remains in the devices of Example 1 relative to the devices of the Example 2. Therefore waste material may be minimized with the devices according to an embodiment as shown in FIGS. 13a, 13b.

TABLE 1 material dispensed in grams in Example 1:

| | | | |
|---|---|---|---|
| 0.2341 | 0.2269 | 0.2454 | 0.2061 |
| 0.2253 | 0.2169 | 0.2215 | 0.2028 |
| 0.2378 | 0.2258 | 0.1942 | 0.208 |
| 0.2344 | 0.2452 | 0.2357 | 0.1666 |
| 0.2346 | 0.246 | 0.2349 | 0.1921 |
| 0.231 | 0.2364 | 0.1982 | 0.1683 |
| 0.2417 | 0.2425 | 0.2212 | 0.1951 |
| 0.2306 | 0.2368 | 0.1728 | 0.1681 |
| 0.2288 | 0.2956 | 0.2095 | |
| 0.2484 | 0.2712 | 0.1718 | |
| 0.2211 | 0.2397 | 0.2074 | |

TABLE 2 material dispensed in grams in Example 2:

| | | | |
|---|---|---|---|
| 0.2200 | 0.2071 | 0.2305 | 0.1824 |
| 0.2087 | 0.2054 | 0.2306 | 0.1905 |
| 0.1935 | 0.2028 | 0.2126 | 0.1935 |
| 0.2076 | 0.1995 | 0.2391 | 0.1749 |
| 0.2033 | 0.228 | 0.2166 | 0.1926 |
| 0.2005 | 0.219 | 0.2189 | 0.1681 |
| 0.2068 | 0.216 | 0.2179 | 0.1699 |
| 0.2003 | 0.1903 | 0.1818 | 0.1585 |
| 0.2047 | 0.2298 | 0.1853 | 0.1708 |
| 0.1992 | 0.2798 | 0.1754 | 0.2242 |

The invention claimed is:
1. A device for providing a dental material, comprising:
a first and a second compartment formed between interconnected layers,
a first and a second dispensing outlet for the first and second compartments, respectively,
a seal separating one of the outlets from the corresponding compartment,
the seal being formed by the layers in an area in which the layers are interconnected but adapted to separate upon forcing a component of the dental material between the layers, and a predetermined fold line along which the device is foldable; wherein the outlets are positioned side by side and spaced from one another by between about 5 mm to 20 mm, when the device is folded by about 180 degree and the compartments at least partially overlap each other.

2. The device of claim 1, comprising a first seal separating the first dispensing outlet from the first compartment, and a second seal separating the second dispensing outlet from the second compartment.

3. The device of claim 2, wherein the first dispensing outlet and the first compartment are connected by a first passageway which is openably closed by the first seal, and wherein the second dispensing outlet and the second compartment are connected by a second passageway which is openably closed by the second seal.

4. The device of claim 1, having for predetermination of the fold line at least one of:
   a perforation;
   a thinned portion;
   at least one generally V-shaped recess.

5. The device of claim 1, wherein the device further comprises a third compartment.

6. The device of claim 1, further comprising a mixing surface on which the dental material can be mixed.

7. The device of claim 6, wherein the mixing surface is provided by one of the layers.

8. The device of claim 6, wherein the mixing surface overlaps with at least one of the compartments of the device.

9. A method of making a device of claim 1 for providing a dental material, comprising the steps of:
   (a) providing a first and a second compartment formed between interconnected layers, a first and a second dispensing outlet for the first and second compartments, respectively, and a seal separating one of the outlets from the corresponding compartment, the seal being formed by the layers in an area in which the layers are interconnected but adapted to separate upon forcing a component of the dental material between the layers;
   (b) providing a first layer;
   (c) providing a component on the first layer; and
   (d) interconnecting a second layer and the first layer and thereby define a compartment that contains the component.

10. The method of claim 9, further comprising the step of predetermining a fold line at the device, by at least one of
   perforating a layer of the device;
   notching a layer of the device; and
   recessing at least one layer of the device.

11. The method of claim 10, further comprising the step of including a hole or a slit in a layer of the device.

12. A kit, comprising a device as specified in claim 1, and an applicator.

13. The kit of claim 12, further comprising a mixing pad.

* * * * *